United States Patent [19]

Cleer, Jr. et al.

[11] 3,998,220
[45] Dec. 21, 1976

[54] CAST VENTING APPARATUS

[76] Inventors: Clarence W. Cleer, Jr., R.D. 2, Box 90, Kane, Pa. 16735; Gerald M. Wilson, c/o Monticola Associates, Howardsville, Va. 24562

[22] Filed: Mar. 4, 1976

[21] Appl. No.: 664,045

Related U.S. Application Data

[63] Continuation of Ser. No. 563,444, March 31, 1975, abandoned.

[52] U.S. Cl. .............................................. 128/91 R
[51] Int. Cl.² ......................................... A61F 5/04
[58] Field of Search ............... 128/91 R, 90, 89, 87, 128/83; 236/49

[56] References Cited
UNITED STATES PATENTS

| | | | |
|---|---|---|---|
| 3,116,731 | 1/1964 | Baxter | 128/91 R |
| 3,656,477 | 4/1972 | Thomas | 128/91 R |
| 3,762,406 | 10/1973 | Wells | 128/91 R |

*Primary Examiner*—John D. Yasko
*Attorney, Agent, or Firm*—Cushman, Darby & Cushman

[57] ABSTRACT

A surgical cast venting device including an upstanding portion extending through a cast wall and having a bore therein, and a disc-shaped portion disposed in the interior of the cast and in cooperation with the upstanding portion. The disc-shaped portion has a central bore extending through one face thereof, and a plurality of generally radially extending fluid passageways extending from the circumference of the disc-shaped portion to the central bore thereof, and in fluid communication with the central bore and the bore in the upstanding portion. The venting device provides for maximum circulation with a minimum potential for irritation of a patient's skin.

9 Claims, 6 Drawing Figures

CAST VENTING APPARATUS

This is a continuation of application Ser. No. 563,444 filed Mar. 31, 1975, now abandoned.

BACKGROUND OF THE INVENTION

The invention relates to a vent means for a surgical (orthopedic) cast, and the assembly of said vent means with a cast and stockingette or the like. It is well known that when a patient has a cast on for any period of time, irritation of the skin covered by the cast may ensue, odors are given off by the portion of the patient covered by the cast, and infection may occur. Therefore, it has been proposed in the prior art to provide ventilation means for casts to facilitate circulation of air to the portion of a patient's body covered by the cast in order to minimize the irritation, etc., thereof. Exemplary prior art proposals are disclosed in U.S. Pat. Nos. 2,704,067, 3,116,731, 3,656,477, and 3,762,406.

None of the above-mentioned prior art proposals have met with a great deal of commercial success or acceptance, undoubtedly due in part to problems associated with the installation thereof and irritation of the patient's skin thereby, and a lack of complete effective circulation. For instance, the vents shown in U.S. Pat. No. 2,704,067 may result in "pouting" of the skin of a patient, and a large number thereof are required to be effective. In one embodiment of the device shown in U.S. Pat. No. 3,116,731 a convex portion of the vent means is provided, which convex portion may make the vent difficult to install, and the tapered point of which may cause irritation to a patient, while in another embodiment thereof maximum ventilation for a given size is not achieved. The device shown in U.S. Pat. No. 3,762,406 directs itself to the problem of "pouting", however an accessory member must be provided therefore, and the area of ventilation is relatively small compared to the total size of the vent means. U.S. Pat. No. 3,656,477 requires the fastening of a cylindrical vent member to a stockingette or the like, and does not provide maximum ventilation for the size of the vent means.

According to the present invention, a vent means for a surgical cast is provided which provides a maximum amount of ventilation for a given size while having the potential of causing a minimum amount of irritation to the skin of the patient. According to the present invention, the vent means consists of a generally disc-shaped portion having two faces thereof disposed in the same general plane, a bore extending through one face of the portion, but not extending through the face thereof adapted to be disposed adjacent the skin of the patient, a plurality of radially extending passageways extending from the circumference of the disc-shaped portion to the central bore, and a generally cylindrical or conical upstanding portion extending from the disc-shaped portion exteriorly of the cast, and having a bore therein in fluid communication with the central bore of the disc-shaped portion and passageways. With such a provision, there is no tendency for the skin of the wearer to be brought up into a ventilation conduit, even upon the application of a vacuum to such conduit, and the chances of skin irritation are minimized. In addition, a maximum amount of ventilation for a given size is provided since the passageways extend generally along the lengths of the cast walls and provide for 360° drawing of air.

It is the primary object of the present invention to provide an improved surgical cast ventilating means. This and other objects of the invention will become clear from an inspection of the detailed description of the invention, and from the appended claims.

DETAILED DESCRIPTION OF THE INVENTION

Figure 1:
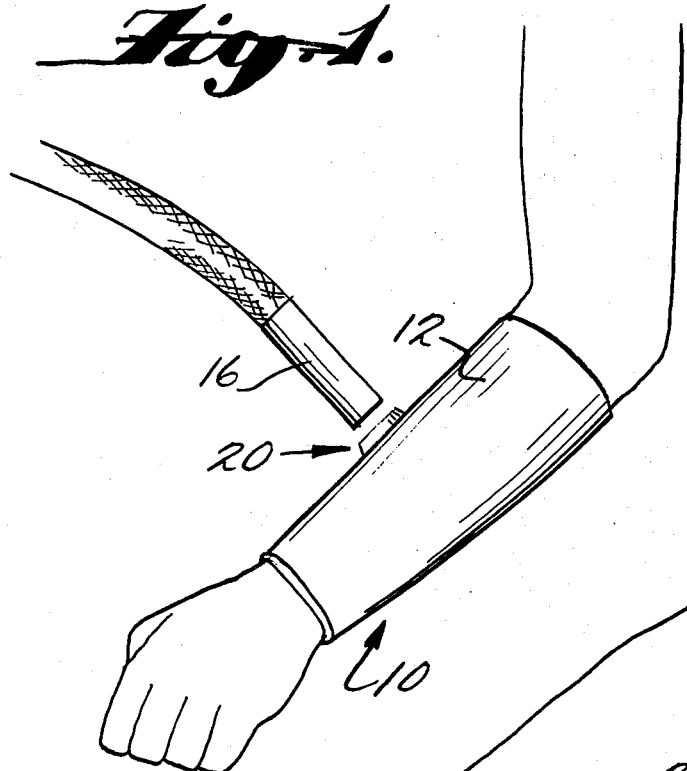
FIG. 1 is a schematic view of an exemplary surgical cast assembly according to the present invention installed on an appendage of a patient.
Figure 2:
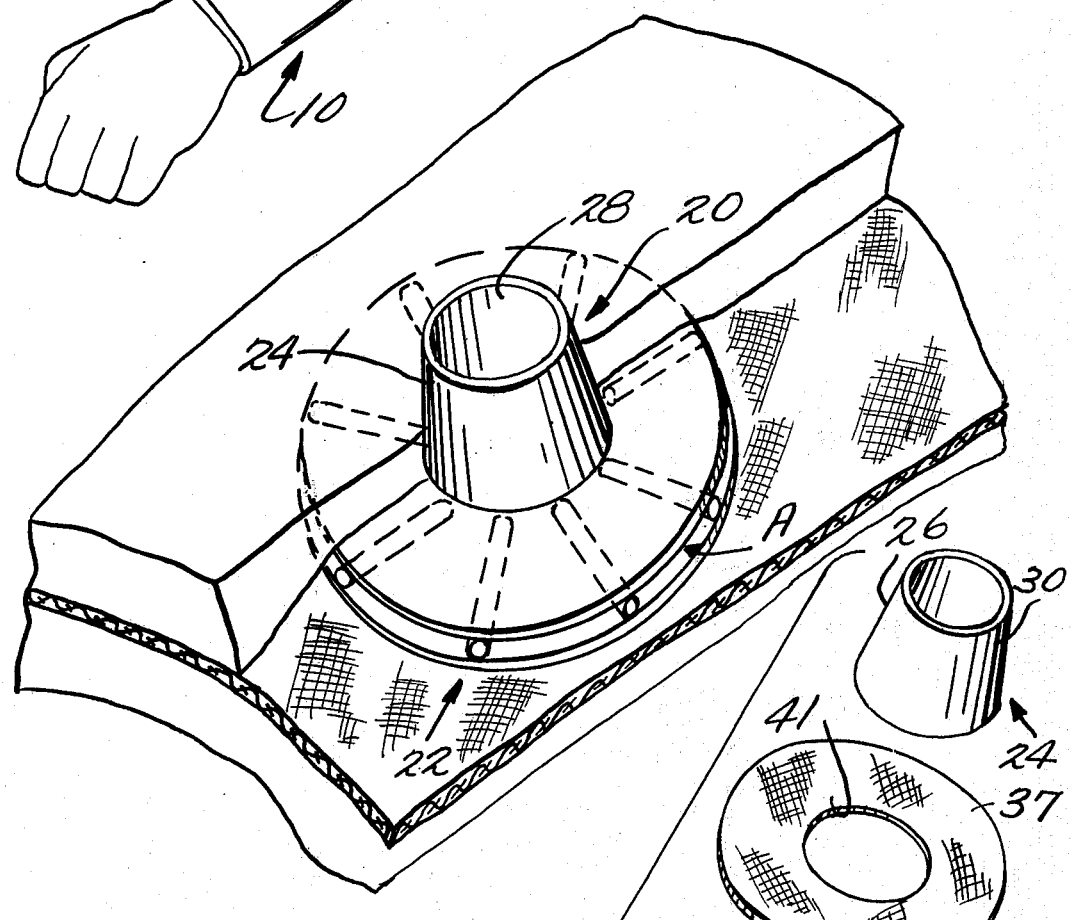
FIG. 2 is a perspective view, with portions of the cast and stockingette cut away for clarity of exemplary ventilating means of the present invention installed in a cast.

A surgical cast assembly according to the present invention is shown generally at 10 in FIG. 1. The assembly includes gauze, a stockingette, or the like 14 surrounding a body appendage and in contact with the skin of the patient, a surgical cast 12 of any suitable material surrounding the stockingette 14, and a vent means 20 having a portion thereof in contact with the stockingette, and extending through the wall of the cast 12 and adapted to be installed in the cast 12 during make-up thereof. The vent means 20 is preferably dimensioned so that it is adapted to be connected to a vacuum cleaner hose 16 or the like. A vacuum supplied by hose 16 results in air being pulled through the cast from around the edges thereof and up through the vent means 20. The use of a vacuum has many advantages over the use of means for blowing air into the cast, as has been suggested by some prior art devices, since the potential for skin irritation is much less, since better circulation can be effected, since medication placed around the cast edges can be drawn into the area covered by the cast thereby and since room air is most often more sterile than air from an air source having air adapted to be blown into the interior of the cast. As shown most clearly in FIG. 2, it is preferred that the vent means extend to a point just beyond the outer surface of the cast 12, and that the vent means have a bore 28 therein dimensioned to receive the end of a vacuum cleaner hose 16.

Figure 3:
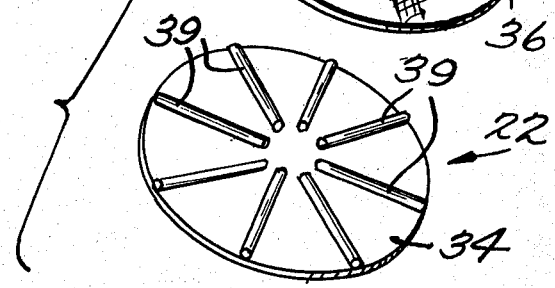
FIG. 3a is an exploded view of an exemplary embodiment of the ventilating means of the present invention.
FIG. 3b is an exploded view of another exemplary embodiment of ventilating means according to the present invention.
Figures 4A, 4B:
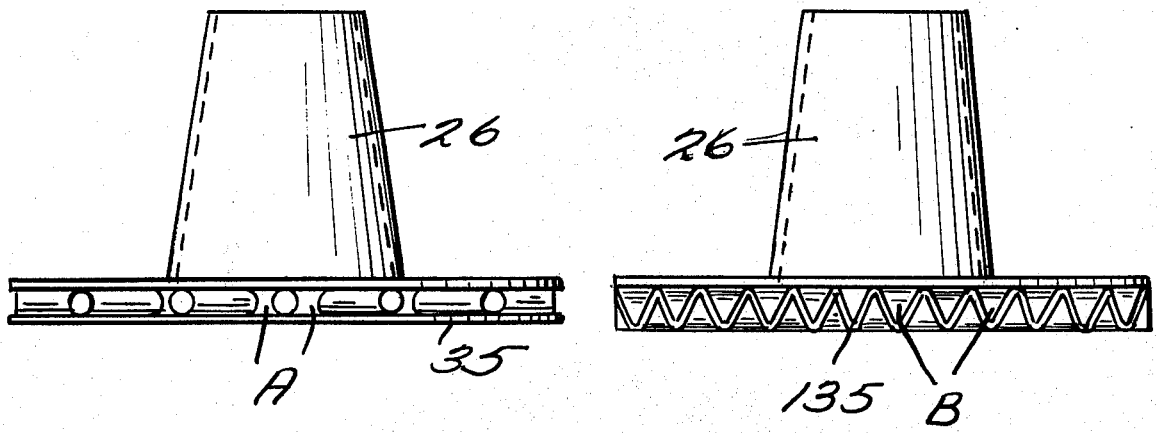
FIG. 4a is a side view of the ventilating means shown in FIG. 3a, and FIG. 4b is a side view of the ventilating means shown in FIG. 3b.

A preferred form of the vent means 20 according to the invention is shown in FIGS. 3a and 4a. The vent means 20 consists of two main components, a disc-shaped portion 22, and a generally tubular upstanding portion 24. The disc-shaped portion 22 may consist of a first plate portion 34 having a surface 35 thereof adapted to be disposed in contact with a stockingette 14 or the like, a second plate portion 36 of generally the same size and shape as the portion 34 (although the first plate portion may be slightly larger) and disposed in substantially the same plane, and a plurality of spacers 39 formed between the plate portions 34 and 36. The second plate portion 36 has a top surface 37 thereof adapted to be disposed toward the surgical cast 12, and has a central bore 41 extending therethrough.

The cooperation of the spacers 39 with plate portions 34 and 36 provides a plurality of radially directed fluid passageways A extending from the circumference of the plate portions 34, 36, into fluid communication with the central bore 41. Either or both of the plate portions 34 and 36, or the surfaces 35 and 37 thereof, may be either flat or slightly curved in order to conform to a body portion, depending upon the size of the device and the particular body portion to which the cast 12 in which it is adapted to be incorporated is to be applied.

The upstanding portion 24 preferably comprises a body member 26 having a bore 28 extending therethrough. The bore 28 is in fluid communication with the central bore 41 and the air passageways A, and provides a conduit from the interior of the cast 12 to the exterior thereof. The body 26 may be conical or cylindrical depending upon the particular use, and rough surface portions 30 or the like — or a concentric flange — may be provided on the exterior thereof to facilitate positive attachment of the cast 12 to the member 26 during make-up of the cast.

It will thus be seen that a vent means 20 has been disclosed that provides for maximum air circulation for a given size thereof and which has a minimum of potential to cause irritation of the skin. Since no bore is formed in the plate portion 34 adapted to be in contact with the stockingette, there is no tendency for portions of the stockingette or the skin to be drawn into a hole, and thus resulting "pouting" or irritation of the skin is avoided. Also, the stockingette 14 cannot interfere with the circulation of air through the passageways A because of their location, and air is drawn therethrough from a 360° area. Also, there are no points on surface 35 which would tend to concentrate stress, therefore irritation of the skin will be further avoided, and no excessive amount of care need be taken during the installation of the vent means in a cast 12.

Figure 3B:
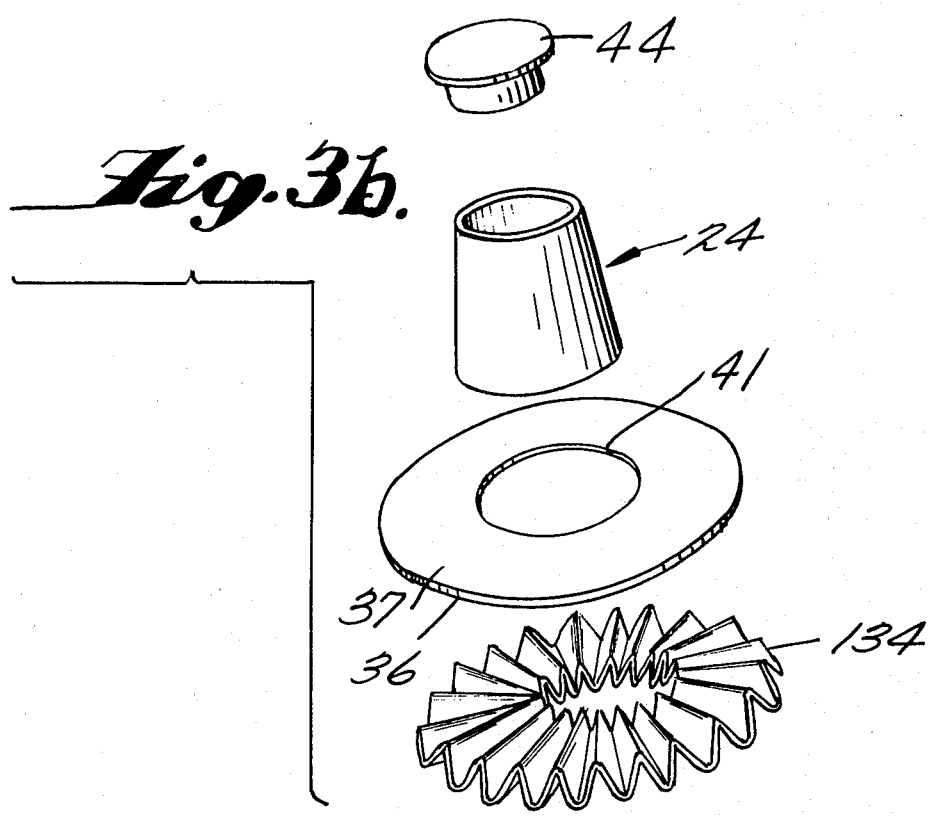

Another preferred embodiment of the vent means of the invention is shown in FIGS. 3b and 4b. In this embodiment, the plate portion 36 and the upstanding portion 24 are the same as in the FIG. 3a embodiment, however no spacers 39 need be provided because of a waffled shape of the first plate portion 134. The plate portion 134 has rounded waffled surface manifestations, whereby a plurality of air passageways B are provided extending from the circumference of the plate 134 radially toward the center thereof, and disposed in fluid communication with the central bore 41 of plate 36. The bottom surface 135 of plate portion 134 may also have a waffled surface to provide for little chance of movement between the vent means 20 and the stockingette 12, while not providing a significant source of irritation to the skin of a patient, as shown in FIG. 4b. Alternatively, the surface 135 could be made smooth and only the surface of portion 134 in contact with plate portion 36 could have the waffled surface manifestations.

While vent means according to the present invention have been shown in exploded views in FIGS. 3a and 3b, and while they have been described as the sum of component parts, it is to be understood that in a preferred form of the invention, all of the components will in fact be integral, formed in a one-step injection molding process. It is preferred that the vent means 20 be formed from a medically approved plastic in order to further reduce the chances of skin irritation therewith.

Also, a plug 44 (or a cap) may be provided for the bore 28 in order to prevent the entry of dirt or water into the cast 12 during some uses thereof.

It will thus be seen that according to the present invention a surgical cast vent means has been provided that provides maximum circulation for a given size and minimum potential for skin irritation, fulfilling the objects of the present invention. While the invention has been herein illustrated and described in what is presently conceived to be the most practical and preferred embodiment, it is to be understood that many modifications may be made thereof within the scope of the invention. For instance, air passageways may be provided by radially extending bores in a solid disc-shaped bottom portion 22, the bores being of any desired size. Other modifications are also possible, thus it is intended that the invention be accorded the broadest scope of the appended claims so as to encompass all equivalent structures and devices.

What is claimed is:

1. A vent means for mounting within a wall of a surgical cast during installation thereof on a patient, said vent means comprising
    a. a generally disc-shaped portion having two faces generally disposed in a common plane,
    b. means defining a central bore in said disc-shaped portion extending generally perpendicular to the faces of said disc-shaped portion, said bore extending through one face of said disc-shaped portion,
    c. means defining a plurality of generally radially extending air passageways in said disc-shaped portion, said passageways extending from the circumference of said disc-shaped portion to said central bore and being in fluid communication therewith, and
    d. an upstanding portion extending from a face of said disc-shaped portion, said upstanding portion having a bore therein in fluid communication with said central bore of said disc-shaped portion, and said upstanding portion adapted to extend from the interior of a cast to the exterior thereof so that a vent is provided from the interior of a cast.

2. A vent means as recited in claim 1 wherein said disc-shaped portion comprises first and second plate portions of generally the same size and shape, said first plate portion being adapted to be disposed adjacent a stockingette or the like and not having said central bore therethrough, and said second plate portion having said central bore therethrough, and wherein said means for defining a plurality of generally radially extending air passageways comprises means for spacing portions of said first and second plate portions from each other.

3. A vent means as recited in claim 2 wherein said spacing means comprise a plurality of spaced rod or bar like members extending generally radially of said plate portions, and disposed therebetween.

4. A vent means as recited in claim 2 wherein the face of said first plate portion adapted to be disposed adjacent a stockingette or the like is slightly curved to generally conform to a body part in which it is in cooperation.

5. A vent means as recited in claim 1 wherein said vent means is formed of an integral piece of plastic material.

6. A vent means as recited in claim 1 wherein said bore in said upstanding portion is so dimensioned that it is adapted to receive a vacuum cleaner hose therein.

7. A surgical cast assembly for installation on a patient, said assembly comprising a. a stockingette or the like adapted to be disposed next to the skin of a patient and surrounding a body portion thereof,
b. a surgical cast of relatively hard material surrounding said stockingette or the like,
c. vent means extending from the interior of said cast to the exterior thereof, said vent means comprising
   i. a generally disc-shaped portion having first and second faces generally disposed in a common plane, said first face being adapted to be disposed against said stockingette or the like,
   ii. means defining a central bore in said disc-shaped portion extending through said second face of said disc-shaped portion,
   iii. means defining a plurality of generally radially extending fluid passageways in said disc-shaped portion, said passageways extending from the circumference of said disc-shaped portion to said central bore and being in fluid communication therewith, and
   iv. an upstanding portion extending from said second face, said upstanding portion having a bore therein in fluid communication with said central bore of said disc-shaped portion, and said upstanding portion adapted to extend from the interior of said cast through a wall thereof to the exterior thereof so that a vent is provided from the interior of said cast to the exterior thereof by said passageways, said central bore, and said upstanding portion bore.

8. An assembly as recited in claim 7 wherein said disc-shaped portion comprises first and second plate portions of generally the same size and shape, said first plate portion having said first face, and said second plate portion having said second face, said central bore extending through said second plate portion, but not said first plate portion, and wherein said means for defining a plurality of generally radially extending air passageways comprises means for spacing portions of said first and second plate portions from each other.

9. An assembly as recited in claim 8 wherein said spacing means comprise a plurality of spaced rod or bar like members extending generally radially of said plate portions, and disposed therebetween.

* * * * *

UNITED STATES PATENT OFFICE
CERTIFICATE OF CORRECTION

Patent No. 3,998,220          Dated December 21, 1976

Inventor(s) Clarence W. Cleer, Jr.

It is certified that error appears in the above-identified patent and that said Letters Patent are hereby corrected as shown below:

In the heading, section [19], the following is deleted:

"et al."

In the heading, section [76], the following is deleted:

"Gerald M. Wilson, c/o Monticola Associates, Howardsville, Va. 24562"

Signed and Sealed this

Twenty-ninth Day of March 1977

[SEAL]

Attest:

RUTH C. MASON
*Attesting Officer*

C. MARSHALL DANN
*Commissioner of Patents and Trademarks*